United States Patent [19]

Pissiotas et al.

[11] 4,402,733

[45] Sep. 6, 1983

[54] HERBICIDALLY ACTIVE 1,2,4-TRIAZIN-5-ONE DERIVATIVES

[75] Inventors: Georg Pissiotas, Lörrach, Fed. Rep. of Germany; Willy Meyer, Riehen, Switzerland; Werner Schwarze, Frankfurt, Fed. Rep. of Germany; Herbert Klenk, Hanau, Fed. Rep. of Germany; Wolfgang Leuchtenberg, Bruchköbel, Fed. Rep. of Germany

[73] Assignees: Ciba-Geigy Corporation, Ardsley, N.Y.; Deutsche Gold- und Silber-Scheideanstalt vormals Roessler, Frankfurt, Fed. Rep. of Germany

[21] Appl. No.: 255,517

[22] Filed: Apr. 20, 1981

Related U.S. Application Data

[63] Continuation of Ser. No. 56,671, Jul. 11, 1979, abandoned, which is a continuation-in-part of Ser. No. 925,063, Jul. 17, 1978, abandoned.

[30] Foreign Application Priority Data

Jul. 20, 1977 [DE] Fed. Rep. of Germany ....... 2732797

[51] Int. Cl.³ .................. A01N 43/64; C07D 253/06

[52] U.S. Cl. .......................................... 71/93; 544/182
[58] Field of Search ............................. 71/93; 544/182

[56] References Cited

U.S. PATENT DOCUMENTS

| 3,629,258 | 12/1971 | Berrer et al. | 71/93 X |
| 3,847,914 | 11/1974 | Dickore et al. | 71/93 X |
| 3,910,909 | 10/1975 | Draber et al. | 544/182 |
| 3,914,224 | 10/1975 | Jewell | 71/93 X |
| 3,966,715 | 6/1976 | Westphal et al. | 71/93 X |

*Primary Examiner*—Catherine L. Mills
*Attorney, Agent, or Firm*—Frederick H. Rabin

[57] ABSTRACT

Herbicidally active derivatives of the formula

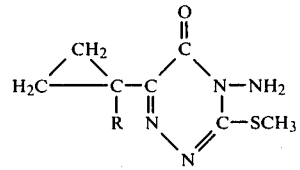

in which R represents methyl, ethyl or n-propyl.

6 Claims, No Drawings

HERBICIDALLY ACTIVE 1,2,4-TRIAZIN-5-ONE DERIVATIVES

This is a continuation of application Ser. No. 056,671, filed on July 11, 1979, now abandoned, which is a continuation-in-part of application Ser. No. 925,063, filed on July 17, 1978, now abandoned.

The present invention relates to three novel 1,2,4-triazinone derivatives, to processes for producing them, to herbicidal compositions containing these 1,2,4-triazin-5-one derivatives as active ingredient, and also to the use of these 1,2,4-triazin-5-one derivatives, or compositions containing them, for controlling undesirable plant growth.

The novel triazinone derivatives are
4-amino-6-(1-methylcyclopropyl)-3-methylthio-1,2,4-triazin-5-one,
4-amino-6-(1-ethylcyclopropyl)-3-methylthio-1,2,4-triazin-5-one,
4-amino-6-(1-n-propylcyclopropyl)-3-methylthio-1,2,4-triazin-5-one.

The novel triazinone derivatives can be produced by a process described by Dornow et al. (Ber. 97, 2173–79, (1964)). According to this process, an alkyl- or aryl-glyoxylic acid is condensed with thiocarbohydrazide to give a 6-aryl- or 6-alkyl-substituted 4-amino-3-thiono-1,2,4-triazin-5-one, and this is subsequently reacted to the 3-methylmercapto derivative by means of a methylation agent. The methylation agent used can be methyl iodide, methyl bromide or dimethyl sulphate in a basic medium. In applying this reaction to the production of the compounds according to the invention, it is necessary however to use as starting material a tert-alkylamide of the corresponding glyoxylic acid. The reaction can be represented by the following reaction equation, wherein $R_1$ represents a tert-alkyl group having 4 to 18 carbon atoms, especially the tert-butyl, tert-amyl or tert-octyl group, and R is methyl, ethyl or n-propyl:

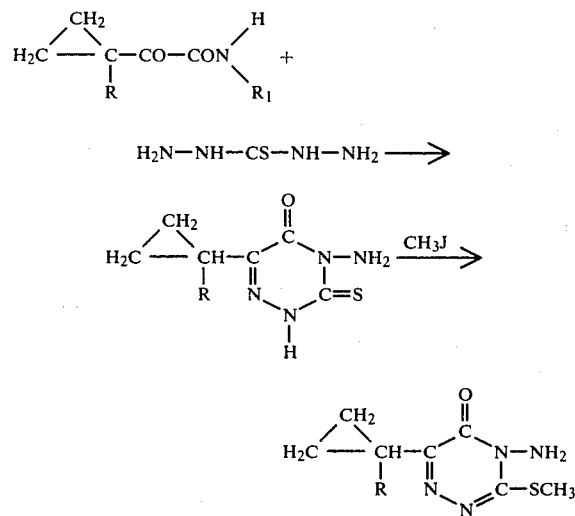

The reactions are performed preferably in polar solvents, such as methanol, ethanol, dimethylformamide, dimethylsulphoxide or water, or in mixtures thereof, at a temperature between 0° C. and the boiling point of the solvents or of mixtures thereof.

The reactions of the thiocarbohydrazide with the tert-alkylamides of (1-alkylcyclopropyl)-glyoxylic acids are performed in the presence of an acid, preferably sulphuric acid or hydrochloric acid, in an amount corresponding to at least the equivalent amount of amide.

The methylation reaction is performed, in a manner known per se, with e.g. methyl iodide or methyl bromide.

The (1-alkylcyclopropyl)-glyoxylic acid tert-alkylamides can be obtained for example by condensation of 1-alkylcyclopropanecarboxylic acid cyanides with a tertiary alcohol or an alkene in an acid medium. This reaction is performed essentially under the conditions of the so-called "Ritter" reaction or "Graf-Ritter" reaction (JACS 70, 4045 (1948); JACS 70, 4048 (1948). The solvent used can be in particular glacial acetic acid or dichloromethane or ether, for example dibutyl ether.

The acylcyanides are for their part obtainable from the corresponding acyl halides. They can be obtained for example by the process according to the German Patent Application No. P 27 08 183.0 by reaction with CuCN, at temperatures between 50° and 180° C., in a mixture of about 1 to 10 parts by weight of an inert carboxylic acid nitrile and about 0.5 to 20 parts by weight of an inert organic solvent, for example dioxane. According to the German Patent Application No. P 27 08 182.9, this production process can be performed also by using a mixture of about 0.1 to 5 parts by weight of an alkali metal cyanide and about 0.05 to 2 parts by weight of a copper-(I)salt, and likewise carrying out the reaction in the presence of an inert carboxylic acid nitrile.

The 1,2,4-triazin-5-one derivatives according to the invention influence plant growth, and they have in particular excellent herbicidal properties. They are especially suitable for controlling weeds, but by virtue of their advantageous desiccating and defoliating activity they can be used also as auxiliaries for increasing yields in crops such as cotton or potatoes.

In combating mono- and dicotyledonous weeds, the active substances exhibit, even when applied in small amounts, an excellent herbicidal action against undesirable plant growth, while clearly having no harmful effect on a wide range of useful crops, and in this respect are surprisingly superior to known 1,2,4-triazin-5-one derivatives which are structurally similar. Even varieties of weeds that are extremely difficult to combat can be controlled by the active substances.

The triazinones according to the invention have very good properties as herbicides against Gramineae, such as millet and millet-like plants, or slender foxtail (Alopecurus sp.)

Various triazinone herbicides are known such, for example, as the compound 4-amino-6-t-butyl-3-methylthio-1,2,4-triazin-5-one (U.S. Pat. No. 4,036,632 and DOS No. 2,361,463). The novel compounds of the present invention differ from these triazinones in pre-emergence and post-emergence tests with average concentrations in that they act much more selectively in some crops of useful plants, for example in crops of maize, soya bean, rye, barley and oats, and also with respect to their effectiveness against Galium aparine.

In the customary formulations, the present compounds can be applied with equal success either after emergence (post-emergence) or especially before emergence (pre-emergence) of the plants. Depending on the purpose of application, the location, the crop, the amount and species of harmful plants, the climatic conditions, etc., the applied amounts of active substances according to the invention can vary within wide limits but are surprisingly low. In light soils, the triazinone derivatives according to the present invention are effective in general in applied amounts from as low as 0.1 kg per hectare, and are applied preferably in amounts of 0.5 to 2.0 kg per hectare; in heavy adsorbtive soils rich in humus, higher amounts are to be applied. In the case of applied amounts of 3.0 kg per hectare and more, the total-herbicidal action of these compounds predominates over the selective action.

The following Examples illustrate the processes for producing the novel compounds. The temperature values are given in degrees Centigrades.

EXAMPLE 1

(a) Production of (1-methylcyclopropyl)-glyoxyl-tert-butyl amide 109 g of (1-methylcyclopropyl)-carboxylic acid cyanide (=1 mol) is added to a mixture of 130 g of t-butanol and 130 ml of methylene chloride. There is then added dropwise at 0° to 5° C., with stirring, 100 g of 98% sulphuric acid; the temperature is subsequently raised to 20° C. and the reaction mixture is stirred for 4 hours. An addition of 18 ml of $H_2O$ is made and stirring is continued for a further 30 minutes. The mixture is afterwards diluted with 500 ml of $CH_2Cl_2$, and the pH value is adjusted with cooling to 6 using aqueous NaOH. The $CH_2Cl_2$ solution is then concentrated by evaporation to leave 181 g (=98.9%) of (1-methylcyclopropyl)-glyoxyl-tert-butylamide, melting point 80° C.

Analysis: calculated: C, 65.5; H, 9.3; N, 7.65%; found: C, 65.2; H, 9.4; N, 7.45%.

(b) Production of 4-amino-6-(1-methylcyclopropyl)-3-mercapto-1,2,4-triazin-5-one 183 g of (1-methylcyclopropyl)-glyoxylic acid tert-butylamide and 112 g of thiocarbohydrazide are added to a mixture of 1 liter of 1 N HCl and 1 liter of ethanol. The mixture is refluxed for 8 hours; it is subsequently cooled and diluted with 2 liters of $H_2O$ and the crystals are filtered off with suction. White crystals having a yellow lustre are obtained and these are dried.

Amount: 152.6 g=77.1% of theory; melting point 137°–138° C.

Analysis: $C_7H_{10}N_4O_2$ (M=198) calculated: C, 42.4; H, 5.05; N, 28.3; S, 16.16%; found: C, 42.2; H, 5.1; N, 28.1; S, 16.1%.

(c) Methylation to give 4-amino-6-(1-methylcyclopropyl)-3-methylthio-1,2,4-triazin-5-one 198 g of compound obtained according to (b) is dissolved in 500 ml of 2 N NaOH, and 500 ml of methanol and 150 g of methyl iodide are added. The reaction mixture is stirred at 20° to 30° C. for 6 hours. The crystals which have formed are filtered off with suction, washed and dried to yield 174.5 g of final product (dried in vacuo at 40° C.); white crystals; melting point 115° to 116° C.; yield 82.3% of theory.

Analysis: (M=212) calculated: C, 45.3; H, 5.7; N, 26.4; S, 15.1%; found: C, 45.3; H, 5.8; N, 26.1; S, 15.3%.

EXAMPLE 2

(a) Production of 1-ethylcyclopropanecarboxylic acid cyanide 90.5 g of 1-ethylcyclopropanecarboxylic acid chloride is stirred in 100 ml of acetonitrile:trichloroethylene (1:1) with 79.3 g of CuCN for 12 hours at 80° C. The cooled suspension is filtered, the filtrate is evaporated to dryness and the residue is distilled to yield 65 g of colourless 1-ethylcyclopropylcarboxylic acid cyanide having a boiling point at 60 millibars of 88° C.

(b) Production of (1-ethylcyclopropyl)-glyoxylic acid tert-butylamide 10 g of $H_2SO_4$ (98%) is added dropwise at 0°–5° C., in the course of 10 minutes, to a solution of 12.3 g of 1-ethylcyclopropanecarboxylic acid cyanide in 13 g of tert-butanol and 13 ml of methylene chloride. The solution is subsequently stirred for 4 hours at room temperature; 2 ml of $H_2O$ is then added and stirring is continued for a further 30 minutes. The pH value of the solution is brought to 6 with 80 ml of ZnNaOH, and the organic phase is separated. After removal of the solvent, the residue is crysrallised out from 50 ml of petroleum ether (b.p. 40° to 65° C.) at 50° C. to thus yield 13.1 g of white crystals of pure (1-ethylcyclopropyl)-glyoxylic acid tert-butylamide having a melting point of 37.5°–39° C.

(c) Production of 3-mercapto-4-amino-6-(1-ethylcyclopropyl)-1,2,4-triazin-5-(4H)-one 9.2 g of thiocarbohydrazide hydrochloride is placed into 65 ml of $H_2O$, and 12.7 g of (1-ethylcyclopropyl)-glyoxylic acid tert-butylamide in 65 ml of ethanol is added. The mixture is stirred for 8 hours at 80° C., in the course of which a proportion of the product precipitates. The suspension is cooled to 20° C.; 130 ml of $H_2O$ is then added and stirring is maintained for 1 hour. The crystals which have precipitated are filtered off, and recrystallized from 50 ml of $CH_3OH$ to yield 8 g of colourless crystals consisting of 3-mercapto-4-amino-6-(1-ethylcyclopropyl)-1,2,4-triazin-5(4H)-one having a melting point of 177°–179° C.

(d) Production of 3-methylthio-4-amino-6-(1-ethylcyclopropyl)-1,2,4-triazin-5(4H)-one 6 g of 3-mercapto-4-amino-6-(1-ethylcyclopropyl)-1,2,4-triazin-5(4H)-one is dissolved in 14.2 ml of 2 N NaOH and 20 ml of $H_2O$ in the cold state. To the solution is added a solution consisting of 4.8 g of methyl iodide and 35 ml of $CH_3OH$. The solution is stirred for 3 hours at room temperature; $H_2O$ is added and the solution is subsequently extracted 3 times with 50 ml of ethyl acetate each time. The organic phase is separated, dried, and evaporated to dryness. The residue (5.7 g) is recrystallized from 0 ml of toluene/petroleum ether (40°–65° C.)=1:1. There is thus obtained 4 g of white crystals of the formula

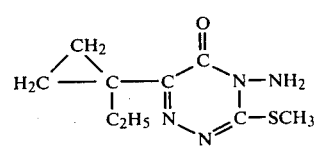

having a melting point of 93°–95° C. The n-propyl derivative can be prepared in a similar manner.

EXAMPLE 3

The herbicidal action of 4-amino-6-(1-methylcyclopropyl)-3-methylthio-1,2,4-triazin-5-one was ascertained by the following tests:

Herbicidal action with application of the active substances before emergence of the plants (pre-emergence method).

Test plants were sown in boxes in a greenhouse: the specimens were cultivated-plants and mono- and dicotyledonous weeds. After sowing, the active substance and a commercial triazinone derivative were sprayed on as aqueous ethanolic dispersions. An evaluation of the effect obtained on the emerged plants was made 28 days after application of the dispersions. The plants during the test were kept uniformly moist. The evaluation was made on the basis of the following scale of six ratings:

1—plants undamaged
2—moderate growth
3—plants ailing
4—slight damage
5—severe damage
6—complete destruction Test compounds:
A: 4-amino-6-t-butyl-3-methylthio-1,2,4-triazin-5-one (previously known)
B: 4-amino-6-(1-methylcyclopropyl)-3-methylthio-1,2,4-triazin-5-one (present invention)

|  | 250 g per hectare | | 500 g per hectare | |
| --- | --- | --- | --- | --- |
| Test plant | A | B | A | B |
| Stellaria media | 6 | 6 | 6 | 6 |
| Sonchus asper | 6 | 6 | 6 | 6 |
| Polygenum persicaria | 6 | 6 | 6 | 6 |
| Plantago lanceolata | 6 | 6 | 6 | 6 |
| Matricaria indodora | 6 | 6 | 6 | 6 |
| Galium aparine | 1 | 6 | 5 | 6 |
| Echinochloa crus-galli | 6 | 6 | 6 | 6 |
| Chenopodium album | 6 | 6 | 6 | 6 |
| Digitaria sanguinalis | 6 | 6 | 6 | 6 |
| Centaurea cyanus | 6 | 6 | 6 | 6 |
| Avena fatua | 6 | 6 | 6 | 6 |
| Amaranthus retroflexus | 6 | 6 | 6 | 6 |
| Agropyron repens | 6 | 6 | 6 | 6 |
| Sinapis alba | 6 | 6 | 6 | 6 |
| Brassica napus | 6 | 6 | 6 | 6 |
| Beta vulgaris | 6 | 6 | 6 | 6 |
| Phaseolus vulgaris | 6 | 6 | 6 | 6 |
| Zea mais | 2 | 5 | 4 | 6 |
| Soja hispida | 5 | 6 | 6 | 6 |
| Triticum aestivum | 6 | 6 | 6 | 6 |
| Secale cereale | 6 | 6 | 6 | 6 |
| Poa annua | 6 | 6 | 6 | 6 |
| Lolium perenne | 6 | 6 | 6 | 6 |
| Mordeum vulgare | 5 | 6 | 6 | 6 |
| Avena sativa | 6 | 6 | 6 | 6 |
| Apera spica venti | 6 | 6 | 6 | 6 |
| Alopycurus myosuroides | 6 | 6 | 6 | 6 |
| Agrostis tenuis | 5 | 6 | 6 | 6 |

EXAMPLE 4

A different pre-emergent test procedure was utilized in this instance to test prior art compound A and compound C: 4-amino-6-(1-ethylcyclopropyl)-3-methylthio-1,2,4-triazin-5-one.

Immediately after sowing the test plants in seed trays, in a greenhouse, the surface of the soil was treated with an aqueous suspension of the active compounds, obtained from 25% strength wettable powder. Different concentrations were used, i.e. 0.5 and 1.0 kg of active substance per hectare. The seed trays were kept in the greenhouse at 22°–25° C. and 50–70% relative atmospheric humidity and the test was evaluated after 3 weeks and the results rated in accordance with the following linear scale:

1 = plants have not germinated or have completely died off
2–8 = intermediate stages of damage
9 = plants undamaged (like untreated control plants).

|  | 0.5 kg/ha | | 1.0 kg/ha | |
| --- | --- | --- | --- | --- |
| Test plant | C | A | C | A |
| Soya | 9 | 9 | 7 | 2 |
| Abutilon Th. | 1 | 1 | 1 | 1 |
| Amarantus retroflexus | 1 | 1 | 1 | 1 |
| Ipomoea cong. | 2 | 7 | 2 | 2 |
| Solanium nigr. | 1 | 1 | 1 | 1 |
| Stellaria media | 1 | 1 | 1 | 1 |
| Sinapis alba | 1 | 1 | 1 | 1 |
| Brachiaria P. | 2 | 2 | 1 | 1 |
| Digitaria sanguinalis | 1 | 1 | 1 | 1 |
| Echinochloa crus-galli | 1 | 1 | 1 | 1 |

It is seen that the compound of the instant invention showed to particular advantage against Ipomoea, a weed which is a serious problem in soya crops. It also showed superior selectivity in soya crop at the higher application rate.

EXAMPLE 5

A pre-emergent test procedure was again conducted pursuant to the procedure of Example 4 and utilizing the evaluation scale of Example 4. Compounds B and C of this application were included as well as
D-4-amino-6-(1-n-propylcyclopropyl)-3-methylthio-1,2,4-triazin-5-one (present invention)
E-4-amino-6-methyl-3-methylthio-1,2,4-triazin-5-one
F-4-amino-6-isopropyl-3-mercapto-1,2,4-triazin-5-one
G-4-amino-6-phenyl-3-methyl-1,2,4-triazin-5-one

|  | 1.0 kg/ha | | | | | 2.0 kg/ha | | | | | 4.0 kg/ha | | | | |
| --- | --- | --- | --- | --- | --- | --- | --- | --- | --- | --- | --- | --- | --- | --- | --- |
| Test plant | B | C | D | E | F | G | B | C | D | E | F | G | B | C | D | E | F | G |
| Alopecurus myosuroides | 1 | 1 | 1 | — | — | 3 | 1 | 1 | 1 | 5 | 9 | 3 | 1 | — | — | 3 | 9 | 2 |
| Digitaria sanguinalis | 1 | 1 | 1 | — | — | 9 | 1 | 1 | 1 | 7 | 9 | 9 | 1 | — | — | 3 | 9 | 8 |
| Echinochloa crus-galli | 1 | 1 | 1 | — | — | 9 | 1 | 1 | 1 | 8 | 9 | 9 | 1 | — | — | 5 | 9 | 9 |
| Sorghum latep. | — | — | 1 | — | — | — | — | — | 1 | 9 | 9 | — | — | — | — | 7 | 9 | — |
| Ipomoea cong. | 1 | 2 | 1 | — | — | 9 | 1 | 1 | 1 | 3 | 9 | 9 | 1 | — | — | 2 | 9 | 9 |
| Galium aparine | 2 | 2 | 3 | — | — | 7 | 1 | 2 | 2 | 7 | 9 | 5 | 1 | — | — | 4 | 9 | 2 |

Once again, the compounds of the instant invention showed to unexpectedly better advantage.

EXAMPLE 6

Post-emergence herbicidal action (contact herbicide)

A number of weeds, both monocotyledonous and dicotyledonous, were sprayed after emergence (in the 4-leaf to 6-leaf stage) with an aqueous emulsion of the active ingredient in dosages of 1 to 4 kg of active substance per hectare, spraying being onto the plants, and the plants were kept at 24°–26° C. and 45–60% relative atmospheric humidity. The test was evaluated 5 days and 15 days after the treatment and the result was rated as in the pre-emergence test of Example 4, in accordance with the same linear scale.

inert to the active substance and not readily combustible.

Furthermore, the active substances according to the invention can be used in the form of solutions. For this purpose, the active substance is dissolved in suitable organic solvents, solvent mixtures or water. The solutions should contain the active substance in a concentration range of 1–20%.

|  | 1.0 kg/ha | | | | | | 2.0 kg/ha | | | | | | 4.0 kg/ha | | | | | |
|---|---|---|---|---|---|---|---|---|---|---|---|---|---|---|---|---|---|---|
| Test plant | B | C | D | E | F | G | B | C | D | E | F | G | B | C | D | E | F | G |
| *Avena fatua* | 1 | 1 | 2 | — | — | 7 | 1 | 1 | 1 | 9 | 9 | 1 | 1 | — | — | 8 | 9 | 1 |
| *Lolium perenne* | 1 | 1 | 1 | — | — | 7 | 1 | 1 | 1 | 9 | 9 | 2 | 1 | — | — | 9 | 9 | 2 |
| *Sida spinosa* | 1 | 1 | 1 | — | — | 2 | 1 | 1 | 1 | 7 | 9 | 1 | 1 | — | — | 6 | 7 | 1 |
| *Sinapis alba* | 1 | 1 | 1 | — | — | 4 | 1 | 1 | 1 | 2 | 4 | 1 | 1 | — | — | 1 | 3 | 1 |
| Abutilon sp. | 1 | 1 | 1 | — | — | — | 1 | 1 | 1 | 3 | 2 | — | 1 | — | — | 1 | 1 | — |
| *Solanum nigrum* | 1 | 1 | 2 | — | — | — | 1 | 1 | 2 | 3 | 5 | — | 1 | — | — | 2 | 1 | — |
| *Chrysanthemum leucum* | 1 | 1 | 1 | — | — | — | 1 | 1 | 1 | 6 | 9 | — | 1 | — | — | 3 | 8 | — |

The compounds of this invention thus also exhibit a pattern of improved performance under post-emergent conditions.

Herbicidal compositions are produced by combining the active substance with suitable carriers and/or distributing agents. This is effected in a manner known per se by the intimate mixing and grinding of the active substance with suitable carriers, optionally with the addition of dispersing agents or solvents which are inert to the active substances. The active substance can be used in the form of dusts, scattering agents, granules (coated granules, impregnated granules or homogeneous granules), wettable powders, pastes, emulsions, solutions or aerosols.

Solid preparations (dusts, scattering agents, granules) are produced by mixing the active substance with the solid carriers. The particle size of the carriers is for dusts advantageously up to about 0.1 mm; for scattering agents about 0.075 to 0.2 mm; and for granules 0.2 mm or coarser. The concentration of active substance in the solid preparations is as a rule 0.5 to 80%. It is possible to add to these mixtures also additives stabilising the active substance, and/or nonionic, anion-active and cation-active substances which improve, for example, the adhesion of the active substance on plants and parts of plants (adhesives and agglutinants), and/or ensure better wettability (wetting agents) and also dispersibility (dispersing agents).

Water-dispersible concentrates of active substances, e.g. wettable powders, pastes and emulsion concentrates, are preparations which can be diluted with water to give the concentration desired. They comprise active substance, carrier, optionally additives stabilising the active substance, surfaceactive substances and antifoaming agents and optionally solvents. The concentration of active substance in these preparations is 5–80%. The wettable powders and pastes are obtained by mixing and grinding the active substance with dispersing agents and pulverulent carriers in suitable devices until the mixture is homogeneous. It is advantageous in some cases to use mixtures of various carriers. Suitable antifoaming agents are, for example, silicones. The active substance is mixed, ground, sieved and strained with the additives mentioned above until the solid constituent in wettable powders has a particle size not exceeding 0.02–0.04 mm, and in pastes not exceeding 0.003 mm. Dispersing agents, organic solvents and water are used to prepare emulsion concentrates and pastes. The solvents have to be virtually odourless, nonphytotoxic,

GRANULATE

The following substances are used to produce a 5% granulate:
5 parts of active substance
0.25 part of epichlorohydrin,
0.25 part of cetyl polyglycol ether having 8 mols of ethylene oxide,
3.50 parts of polyglycol ("Carbowax" ®), and
91 parts of kaolin (particle size 0.3–0.8 mm).

The active substance is mixed with epichlorohydrin and the mixture is dissolved in 6 parts of acetone, and the polyglycol and cetyl polyglycol ether are then added. The solution thus obtained is sprayed onto kaolin and the acetone is subsequently evaporated off in vacuo.

WETTABLE POWDERS

The following constituents are used to produce (a) a 50%, (b) a 25% and (c) a 10% wettable powder:

(a)

50 parts of active substance,
5 parts of sodium dibutylnaphthalene sulphonate,
3 parts of naphthalenesulphonic acid/phenolsulphonic acid/formaldehyde condensate 3:2:1,
20 parts of kaolin, and
22 parts of Champagne chalk;

(b)

25 parts of the active substance mentioned above,
5 parts of the sodium salt of oleyl methyl tauride,
2.5 parts of naphthalenesulphonic acid/formaldehyde condensate,
0.5 part of carboxymethyl cellulose,
5 parts of neutral potassium aluminum silicate, and
62 parts of kaolin; and (c)

10 parts of the active substance mentioned above,
3 parts of a mixture of the sodium salts of saturated fatty alcohol sulphates,
5 parts of naphthalenesulphonic acid/formaldehyde condensate, and
82 parts of kaolin.

The stated active substance is absorbed onto the respective carriers (kaolin and chalk), and the material is subsequently mixed and ground. Wettable powders having excellent wetting and suspension properties are obtained. Suspensions of the concentration desired can be obtained from wettable powders of the above kind by diluting the powders with water. These suspensions can be used to control weeds and wild grasses in cotton crops.

PASTE

The following substances are used to produce a 45% paste:
45 parts of active substance,
5 parts of sodium aluminium silicate,
14 parts of cetyl polyglycol ether having 8 mols of ethylene oxide,
1 part of cetyl polyglycol ether having 5 mols of ethylene oxide,
2 parts of spindle oil,
10 parts of polyglycol (Carbowax ®), and
23 parts of water.

The active substance is intimately mixed and ground with the additives in devices suitable for the purpose. Suspensions of the concentration desired can be prepared by diluting the resulting paste with water.

EMULSION CONCENTRATE

The following constituents are mixed together to produce a 10% emulsion concentrate:
10 parts of active substance,
15 parts of oleyl polyglycol ether having 8 mols of ethylene oxide, and
75 parts of isophorone (3,5,5-trimethylcyclohex-2-en-1-one).

This concentrate can be diluted with water to give emulsions of a suitable concentration. Emulsions of this type are suitable for controlling weeds in cultivated crops, for example in crops of soya beans and potatoes.

We claim:

1. A 1,2,4-triazin-5-one derivative selected from the group consisting of 4-amino-6-(1-methylcyclopropyl)-3-methylthio-1,2,4-triazin-5-one, 4-amino-6-(1-ethylcyclopropyl)3-methylthio-1,2,4-triazin-5-one and 4-amino-6-(1-n-propylcyclopropyl)-3-methylthio-1,2,4-triazin-5-one.

2. A herbicidal composition comprising a herbicidally effective amount of a compound according to claim 1, together with a suitable carrier therefor.

3. A method for combatting weeds in crops of cultivated plants which comprises applying to said weeds or the locus thereof a herbicidally effective amount of a compound according to claim 1.

4. The 1,2,4-triazin-5-one derivative of claim 1 which is 4-amino-6-(1-methylcyclopropyl)-3-methylthio-1,2,4-triazin-5-one.

5. The 1,2,4-triazin-5-one derivative of claim 1 which is 4-amino-6-(1-ethylcyclopropyl)-3-methylthio-1,2,4-triazin-5-one.

6. The 1,2,4-triazin-5-one derivative of claim 1 which is 4-amino-6-(1-n-propylcyclopropyl)-3-methylthio-1,2,4-triazine-5-one.

* * * * *